US008919959B2

(12) United States Patent
Makihira

(10) Patent No.: US 8,919,959 B2
(45) Date of Patent: Dec. 30, 2014

(54) PHOTOGRAPHING APPARATUS AND IMAGE PROCESSING METHOD

(75) Inventor: Tomoyuki Makihira, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 345 days.

(21) Appl. No.: 13/404,219

(22) Filed: Feb. 24, 2012

(65) Prior Publication Data
US 2012/0229762 A1 Sep. 13, 2012

(30) Foreign Application Priority Data

Mar. 10, 2011 (JP) ................................. 2011-052287

(51) Int. Cl.
*A61B 3/14* (2006.01)
*G06T 7/20* (2006.01)
*A61B 3/10* (2006.01)

(52) U.S. Cl.
CPC ....... *A61B 3/102* (2013.01); *G06T 2207/10101* (2013.01); *G06T 2207/30041* (2013.01); *G06T 7/2046* (2013.01)
USPC ......................................... 351/209; 351/206

(58) Field of Classification Search
CPC ........... A61B 3/113; A61B 3/12; A61B 3/143
USPC ................................................. 351/206, 209
See application file for complete search history.

(56) References Cited

U.S. PATENT DOCUMENTS

| 6,325,512 | B1 | 12/2001 | Wei | |
|---|---|---|---|---|
| 7,458,684 | B2 | 12/2008 | Fukuma et al. | |
| 7,510,282 | B2 | 3/2009 | Ueno et al. | |
| 2007/0070295 | A1* | 3/2007 | Tsukada et al. | 351/206 |
| 2007/0159596 | A1* | 7/2007 | Fukuma et al. | 351/206 |
| 2008/0024721 | A1 | 1/2008 | Ueno et al. | |
| 2010/0110171 | A1 | 5/2010 | Satake | |
| 2010/0110172 | A1* | 5/2010 | Satake | 348/78 |
| 2011/0176110 | A1* | 7/2011 | Bublizt et al. | 351/206 |
| 2012/0002166 | A1 | 1/2012 | Tomatsu et al. | |
| 2012/0321166 | A1* | 12/2012 | Kitamura et al. | 382/131 |

FOREIGN PATENT DOCUMENTS

| CN | 100998493 A | 7/2007 |
|---|---|---|
| EP | 1602322 A1 | 12/2005 |
| EP | 1 882 445 A2 | 1/2008 |
| EP | 2 184 004 A1 | 5/2010 |

(Continued)

OTHER PUBLICATIONS

Nov. 20, 2012 European Communication in European Patent Appln. No. 12158013.8.

(Continued)

*Primary Examiner* — Jordan Schwartz
(74) *Attorney, Agent, or Firm* — Fitzpatrick, Cella, Harper & Scinto

(57) ABSTRACT

To provide appropriate position information to a tomographic image of fundus in an ophthalmology apparatus for acquiring fundus tomographic images and fundus images. A calculation unit that calculates movement information of an eyeball from fundus images and a matching unit that matches the calculated movement information with fundus tomographic images are provided to the ophthalmology apparatus including a fundus image pickup apparatus to acquire an amount of movement of an eye to be inspected, wherein the calculation unit calculates movement information for the fundus tomographic image having no movement information to be further matched from the movement information of tomographic images before and after the fundus tomographic image so that movement information to be matched with the fundus tomographic image originally having no movement information is calculated from the movement information of tomographic images before and after the fundus tomographic image.

19 Claims, 6 Drawing Sheets

(56) References Cited

FOREIGN PATENT DOCUMENTS

| JP | 2004-512125 | A  | 4/2004 |
|----|-------------|----|--------|
| JP | 2007-185243 | A  | 7/2007 |
| JP | 3976678     | B2 | 9/2007 |
| WO | WO 2010/037485 | A1 * | 4/2010 |

OTHER PUBLICATIONS

Mar. 5, 2014 Chinese Official Action in Chinese Patent Appln. No. 201210064118.1.

* cited by examiner

PHOTOGRAPHING APPARATUS AND IMAGE PROCESSING METHOD

BACKGROUND OF THE INVENTION

1. Field of the Invention

The present invention relates to a photographing apparatus and an image processing method. In particular, the present invention relates to a photographing apparatus that uses eyeball movement information and reflects the eyeball movement information in a tomographic image of fundus, and an image processing method.

2. Description of the Related Art

In recent years, an Optical Coherence Tomography (OCT) apparatus capable of acquiring a tomographic image of fundus has attracted attention. One of the reasons for the attention is that an internal structure of fundus that cannot be observed by other apparatuses can be diagnosed in a non-invasive manner. Among others, a Fourier Domain-Optical Coherence Tomography (FD-OCT) apparatus capable of photographing at high speed and having a track record is the focus of attention on the market. The OCT apparatus is equipped with a fundus camera and Scanning Laser Ophthalmoscope (SLO) in the same apparatus and can acquire an OCT image of a desired area by displaying which area of fundus to be scanned by OCT.

On the other hand, higher quality of an OCT image is demanded to detect a micro tumor or abnormal conditions in terms of early diagnosis and early treatment. To achieve higher quality, an apparatus (Japanese Patent Application Laid-Open No. 2004-512125 (Patent Registration No. 3976678)) that causes an OCT beam to follow eyeball movement is disclosed.

Japanese Patent Application Laid-Open No. 2004-512125 adds a device to detect eyeball movement to the OCT apparatus. The device acquires an OCT image of a desired location by following an optic disk of fundus and controlling the OCT scanner in real time.

With the realization of speedup of the FD-OCT, the time needed to acquire an OCT image may be faster than the time needed to acquire eyeball movement information. Such an apparatus has a problem that position information corresponding to all OCT images is not necessarily obtained.

According to the configuration of Japanese Patent Application Laid-Open No. 2004-512125 described above, eyeball movement can be followed at high speed, but a tracking device needs to be added, leading to a larger apparatus in size and requiring expensive devices such as a scanner.

If images are superimposed in an OCT apparatus having a tracking device in which the acquisition rate of a tracking image is slower than the acquisition rate of an ordinary OCT image, an OCT image without position information is present also a problem of low precision of image superimposition due to micro saccade specific to the eyeball is caused.

SUMMARY OF THE INVENTION

To solve the above problems, a photographing apparatus according to the present invention includes a fundus image pickup unit that photographs fundus images of an eye to be inspected, a tomographic image pickup unit that photographs tomographic images of the eye to be inspected, a calculation unit that calculates movement information of the eye to be inspected from the fundus images, and a matching unit that matches the calculated movement information and the tomographic images, wherein the calculation unit calculates the movement information of a tomographic image which does not correspond to the movement information, on the basis of the movement information of a plurality of tomographic images which correspond to the movement information and are temporally close to the tomographic image which does not correspond to the movement information.

To solve the above problems, an image processing method according to the present invention photographs fundus images and tomographic images of an eye to be inspected, calculates movement information of the eye to be inspected from the fundus images, matches the calculated movement information and the tomographic images, and calculates the movement information of a tomographic image which does not correspond to the movement information, on the basis of the movement information of a plurality of tomographic images which correspond to the movement information and are temporally close to the tomographic image which does not correspond to the movement information.

According to the present invention, eyeball movement information can be calculated even if movement information of an eye to be inspected cannot be acquired from a fundus image and so appropriate image processing can be performed.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

First Embodiment

The first embodiment of the present invention will be described below.

In the present embodiment, a case where a superimposed image (for example, an image obtained by averaging a plurality of OCT images) of high-quality OCT images is acquired by containing an internal fixation lamp, using the SLO to acquire a fundus image, determining the amount of movement of the eyeball from SLO images acquired by the SLO, and reflecting the result in processing of OCT images acquired by an OCT apparatus will be described.

(Configuration of OCT Image Pickup Unit)

Figure 1:
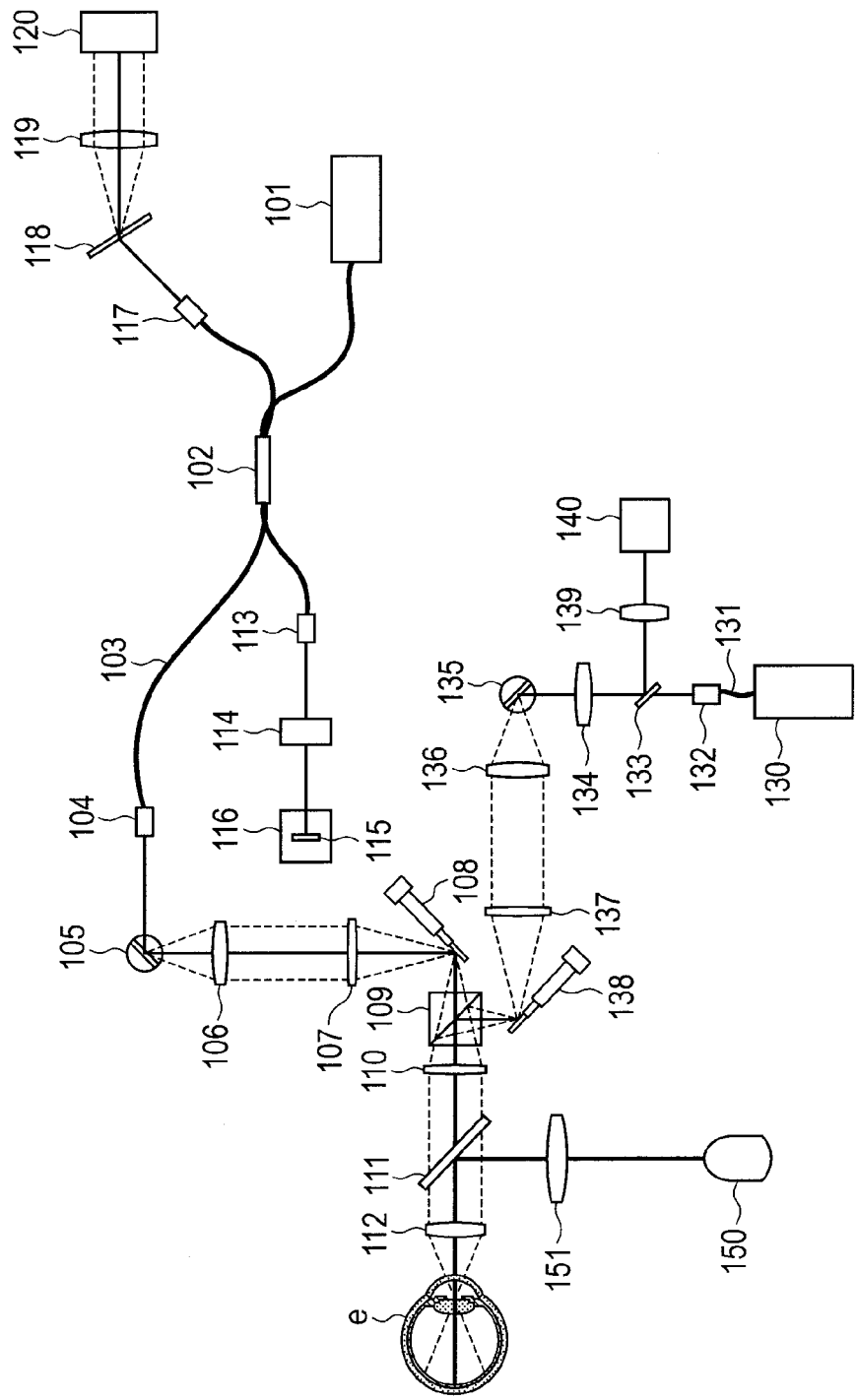
FIG. 1 is a schematic diagram of an optical system configuration of an ophthalmology apparatus according to a first embodiment of the present invention.

FIG. 1 is a schematic diagram of an optical system configuration of a photographing apparatus according to the present embodiment.

First, the optical system configuration of a tomographic image acquisition unit to acquire a tomographic image of an eye to be inspected or an OCT image pickup unit functioning as an image pickup unit in the present invention will be described by using FIG. 1.

A low coherent light source 101 is used as the light source. As the light source 101, a Super Luminescent Diode (SLD) light source or an Amplified Spontaneous Emission (ASE) light source can suitably be used. As the low coherent light, the wavelength near 850 nm or 1050 nm is suitably used for fundus photographing. In the present embodiment, an SLD light source of the center wavelength of 840 nm and wavelength half width of 45 nm is used.

Low coherent light emitted from the low coherent light source 101 enters a fiber coupler 102 through an optical fiber and is divided into a measuring light (OCT beam) and a reference light. An interferometer configuration using a fiber is shown here, but a configuration in which a beam splitter is used in a spatial light optical system may also be adopted.

The measuring light is emitted from a fiber collimator 104 as parallel light via a fiber 103. The emitted measuring light further passes through an OCT scanner (X) 108 after going through an OCT scanner (Y) 105 and relay lenses 106, 107 and, after transmission of a dichroic beam splitter 109, passes through a scan lens 110, a dichroic mirror 111, and an ocular 112 to shine on an eye to be inspected e. A galvano-scanner is used as the OCT scanners (X) 108 and (Y) 105. The measuring light in the eye to be inspected e is reflected by the retina and returns to the fiber coupler 102 by passing through the same optical path.

The reference light is guided from the fiber coupler 102 into a fiber collimator 113 and converted into parallel light before being emitted. The emitted reference light passes through dispersion corrected glass 114 and is reflected by a reference mirror 116 on an optical path length variable stage 115. The reference light reflected by the reference mirror 116 returns to the fiber coupler 102 by passing through the same optical path.

The returned measuring light and reference light are combined by the fiber coupler 102 and guided into a fiber collimator 117. Here, the combined light will be called an interference light. A spectroscope includes the fiber collimator 117, a grating 118, a lens 119, and a linear sensor 120. The interference light is measured by the spectroscope as intensity information for each wavelength. The intensity information for each wavelength measured by the linear sensor 120 is transferred to a CPU 201 described later where the intensity information is formulated as a tomographic image of the eye to be inspected e.

(Configuration of SLO Image Pickup Unit)

Next, the optical system configuration of a fundus image acquisition unit of the present invention to acquire a fundus image of an eye to be inspected or an SLO image pickup unit functioning as an image pickup unit will be described by similarly using FIG. 1.

As a laser light source 130, a semiconductor laser or SLD light source can suitably be used. The wavelength to be used is not limited if the light source has a wavelength that can be separated from the low coherent light source 101 for OCT by the dichroic beam splitter 109, but a near-infrared wavelength band of 700 nm to 1000 nm favorable for image quality of fundus images is suitably used. In the present embodiment, a semiconductor laser of the wavelength of 760 nm is used. A laser beam (SLO beam) emitted from the laser light source 130 is emitted from a fiber collimator 132 as parallel light via a fiber 131 and guided into an SLO scanner (Y) 135 via a perforated mirror (ring mirror) 133 and a lens 134. The laser beam passes through an SLO scanner (X) 138 via lenses 136, 137 and is reflected by the dichroic beam splitter 109 before entering the target eye to be inspected e. The dichroic beam splitter 109 is configured to reflect an SLO beam while allowing an OCT beam to transmit. Like the OCT image pickup unit, a galvano-scanner is used as the scanner in the SLO image pickup unit. The SLO beam that has entered the eye to be inspected e irradiates the fundus of the eye to be inspected e with the beam. The beam is reflected or scattered by the fundus of the eye to be inspected e and returns to the ring mirror 133 by passing through the same optical path. The position of the ring mirror 133 is conjugate with the pupil position of the eye to be inspected e and light passing through a periphery of the pupil of back-scattered light of a beam with which the fundus is irradiated is reflected by the ring mirror 133 to form an image on an avalanche photodiode (APD) by a lens 139. Based on intensity information of the APD 140, a plane image of the fundus is formulated by the CPU 201. In the present embodiment, the SLO that obtains a fundus image by irradiating the fundus with a beam of some spot radius and scanning is used, but the configuration of a Line SLO (LSLO) using a line beam may also be used.

(Internal Fixation Lamp)

In the present embodiment, an internal fixation lamp to cause the eye to be inspected e to gaze to stabilize flicks. Like the OCT image pickup unit and the SLO image pickup unit, the internal fixation lamp will be described by using FIG. 1.

A light emitting diode (LD) is used as a light source 150 used for the internal fixation lamp. The lighting position of the light emitting diode is changed by fitting to the region to be photographed through control of the CPU 201 described later. A beam emitted from the light source in the wavelength of 500 nm of the light emitting diode 150 passes through a lens 151 and the dichroic mirror 111 before the eye to be inspected e being irradiated with the beam. The dichroic mirror 111 is positioned between the scan lens 110 and the ocular 112 and divides the wavelength into light of a short wavelength (about 500 nm) and an OCT beam and SLO beam (700 nm or longer).

(Unit Configuration)

Figure 2:
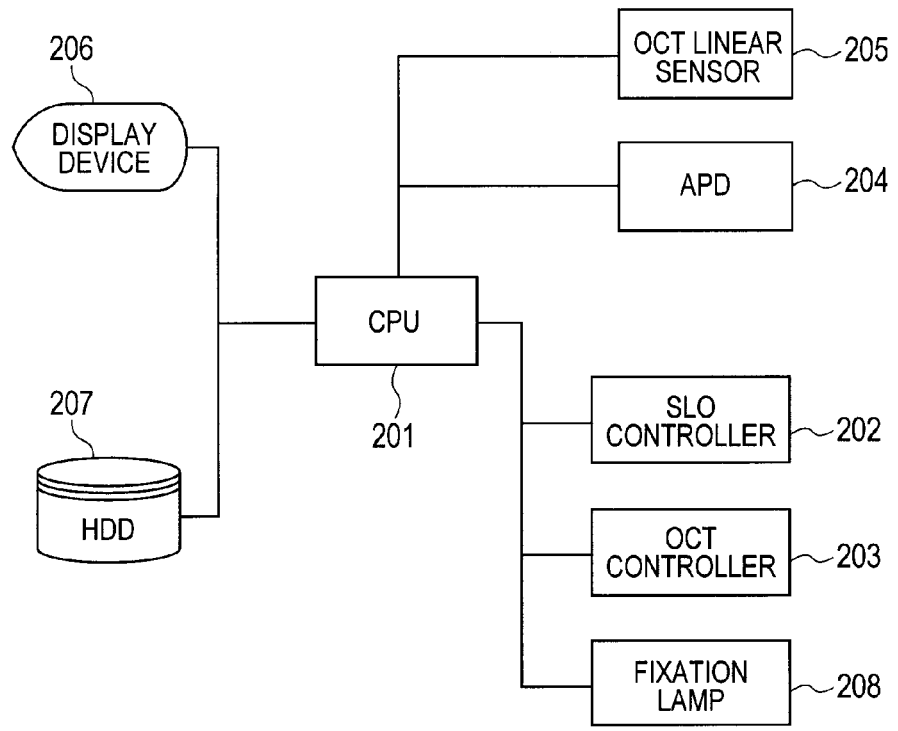
FIG. 2 is a schematic diagram of a functional system of an apparatus according to the first embodiment of the present invention.

FIG. 2 shows a functional system used by the present embodiment. The functional system includes the CPU 201 that controls the whole apparatus, controllers 202, 203 controlling the SLO image pickup image and the OCT image pickup unit respectively, a fixation lamp 208, an APD 204 (140) and a linear sensor 205 (120) each acquiring SLO images and OCT images, a display unit 206 that displays a system state and photographed images, and a recording unit 207 that records fundus images and photographing conditions. To photograph the fundus, the fixation lamp 208 is controlled to cause the eye to gaze at the fixation lamp to be able to photograph a desired fundus area, respective photographing conditions are issued to the controllers 202, 203 by the CPU 201, and each scanner is driven to photograph the fundus. After the fundus being photographed, an image thereof is sent from the APD 204 and the linear sensor 205 to the CPU 201 and the image being processed, the image is displayed by the display unit 206 and stored in the recording unit 207 at the same time/or later.

(Eyeball Movement)

Figure 3:
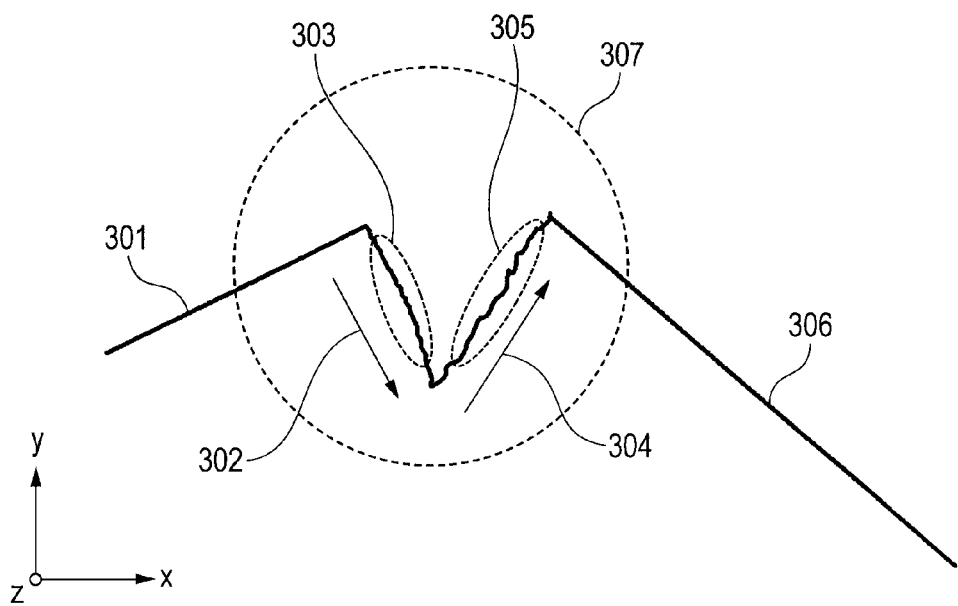
FIG. 3 is a schematic diagram of eyeball movement according to the first embodiment and a second embodiment of the present invention.

If the amount of movement of the eyeball in the direction of the fundus plane is measured, the movement shown as a solid line in FIG. 3 is detected. During the measurement, the fixation lamp is controlled in such a way that a gazing region of the subject is around a dotted line 307. Generally, the movement is roughly divided as follows: micro saccades 301, 306 that are high-speed linear movements, drifts 302, 304 that are somewhat slower movements, and tremors 303, 305 that vibrate microscopically at high speed during the drifts. The movement speed and frequency of the movement depend on each individual and the micro saccade is said to be at 3 mm/sec, which is an order of magnitude faster than drifts at about 100 μm/sec. The period of micro saccade is about once or twice in three seconds. Drifts always continue to move. Tremors are small movements of 5 μm in amplitude and move in a period of about 100 Hz.

(Concrete Example)

The above apparatus is used, the OCT image pickup unit is configured to be able to acquire an image of 8×3 mm$^2$ at an acquisition rate of tomographic images of 40 Hz, and the SLO image pickup unit is configured to be able to acquire an image of 8×6 mm$^2$ at an acquisition rate of fundus images of 20 Hz.

Figure 4:
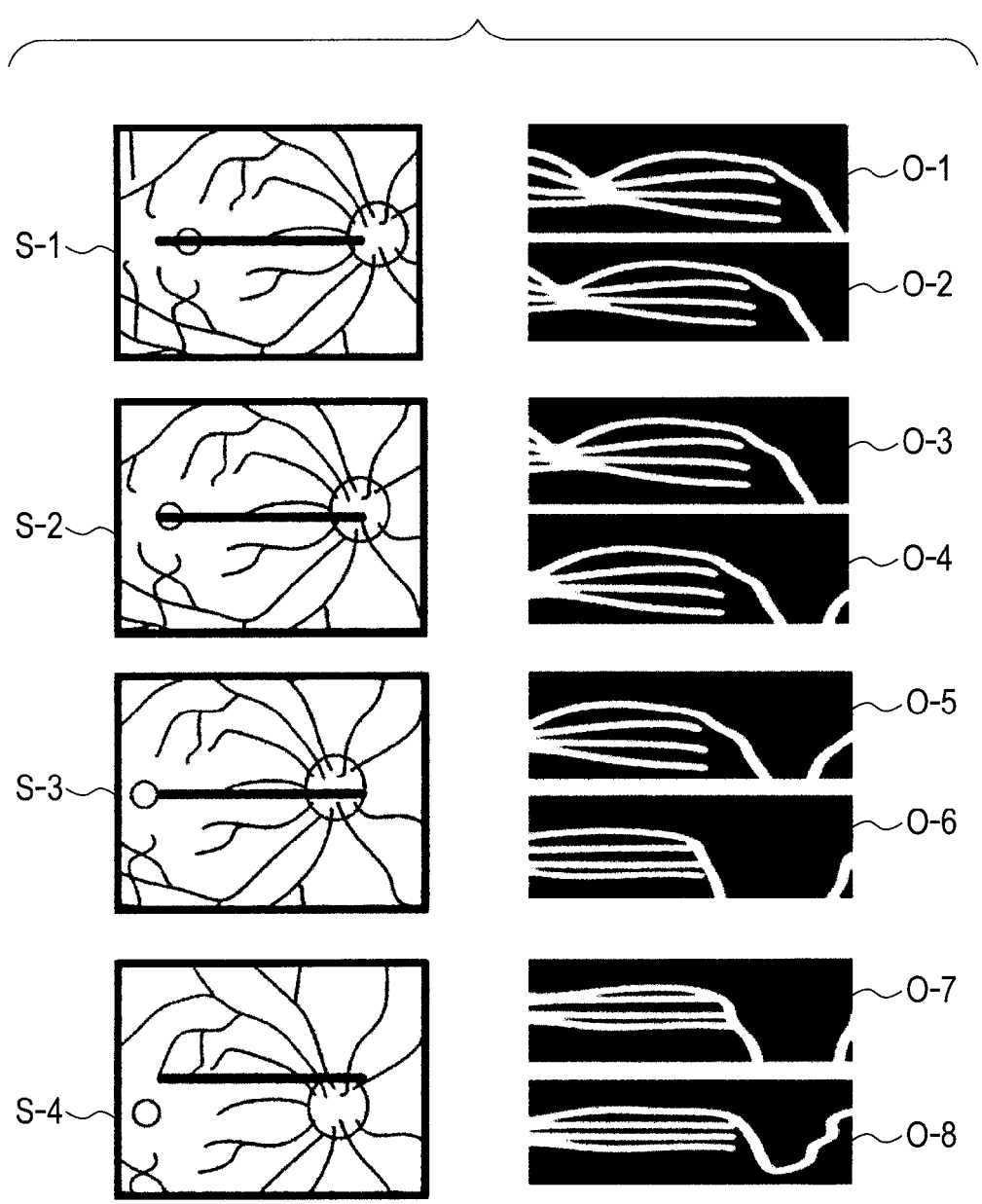
FIG. 4 is a schematic diagram of SLO images and OCT images according to the first embodiment of the present invention.

Images acquired by each image pickup unit are shown in FIG. 4. Two OCT images can be acquired in the time in which one SLO image is acquired.

After the measurement is completed, the movement of the eyeball is calculated from each of SLO images S-1 to S-4 to S-n (n: integer) in a plurality of images obtained at different times. According to the calculation method, the amount of movement of the eyeball is calculated from images of S-1 and S-2, which are SLO images, by the optical flow. Next, the amount of movement of the eyeball is also calculated from SLO images S-2 and S-3 and the above procedure is subsequently repeated to calculate the amount of movement of the eyeball as movement information. The step of calculating movement information from a plurality of fundus images is executed by a portion of the CPU 201 functioning as a calculation unit.

It is assumed that the OCT image corresponding to the SLO image S-1 is O-2 and the OCT image corresponding to the SLO image S-2 is O-4. Thus, the OCT image corresponding to the SLO image S-n is O-2n. A plurality of OCT images is also acquired at different times.

When OCT images are superimposed, an OCT image whose position is present based on an SLO image is superimposed in a position in consideration of the amount of movement of the eyeball. At this point, the calculated movement information and SLO images which from the information is obtained are matched with corresponding OCT images. The operation of matching is performed by a portion of the CPU 201 functioning as a matching unit. In other words, the matching unit matches movement information and tomographic images. If position information in the y direction exceeds a preset reference value, images are considered to be inappropriate as images to be superimposed and are not used for superimposition. Further, the OCT image O-(2n−1) for which the corresponding SLO image is not present is superimposed by using an average value of position information of the previous and subsequent SLO images S-(2n−1)−1 and S-(2n−1)+1 and reflecting the position information.

Movement information to be matched with non-matched OCT images is calculated by the calculation unit using movement information temporally close to an OCT image that can be matched as described above, that is, matched with OCT images acquired immediately before and after the time when the applicable image is acquired. That is, the calculation unit calculates movement information of non-matched tomographic images on the basis of movement information of, among tomographic images matched with movement information, tomographic images temporally close to tomographic images non-matched with movement information. If the acquisition rate of SLO images and the acquisition rate of OCT images are significantly different and OCT images that cannot be matched with movement information are still present, any OCT image that is temporally before or after such non-matched OCT images and is matched may be used.

Thus, the superimposition of OCT images for which no position information is present can achieve higher quality of images by using position information determined by carrying out a calculation from images for which position information is present. The superimposition of a plurality of tomographic images is performed by actually superimposing and combining OCT images by a portion of the CPU 201 functioning as a combining unit.

Second Embodiment

In the present embodiment, an example in which a high-quality OCT image is obtained by containing an internal fixation lamp, an SLO image pickup unit, and an OCT image pickup unit, detecting movement of the eyeball from SLO images, interpolating the amount of movement of the eyeball, determining position information for all OCT images, selecting OCT images to be used based on micro saccade and the amount of movement in the y direction (value of Δy), and superimposing OCT images in consideration of the movement of the eyeball.

The apparatus configuration is the same as in the first embodiment and thus, a description thereof will not be repeated.

Figure 5:
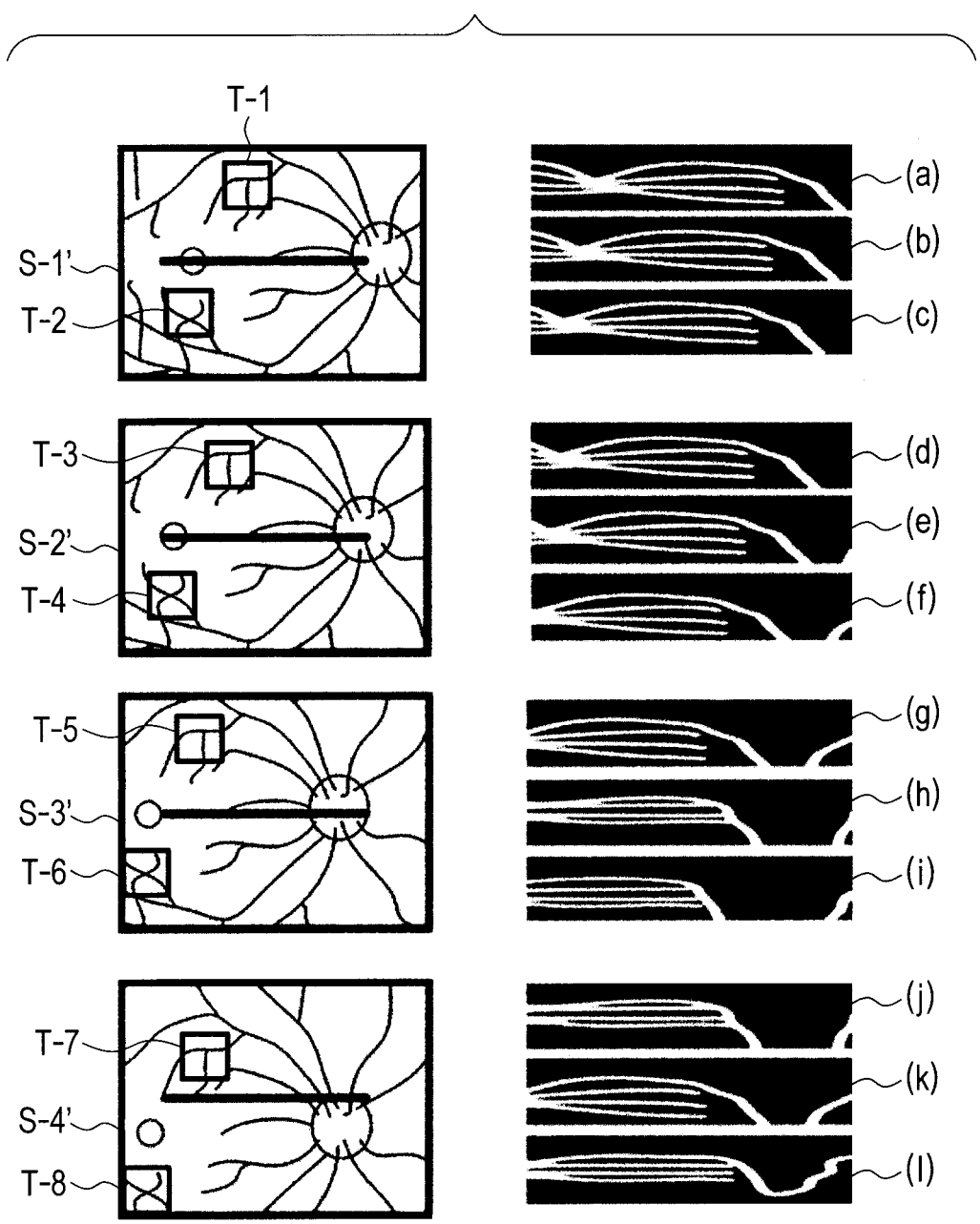
FIG. 5 is a schematic diagram of SLO images and OCT images according to the second embodiment of the present invention.

In the present embodiment, the OCT image pickup unit is configured to be able to acquire images of 8×3 mm$^2$ at 60 Hz and the SLO image pickup unit is configured to be able to acquire images of 8×6 mm$^2$ at 20 Hz. Images acquired by each image pickup unit are shown in FIG. 5. Three OCT images can be acquired in the time in which one SLO image is acquired.

Figure 6:
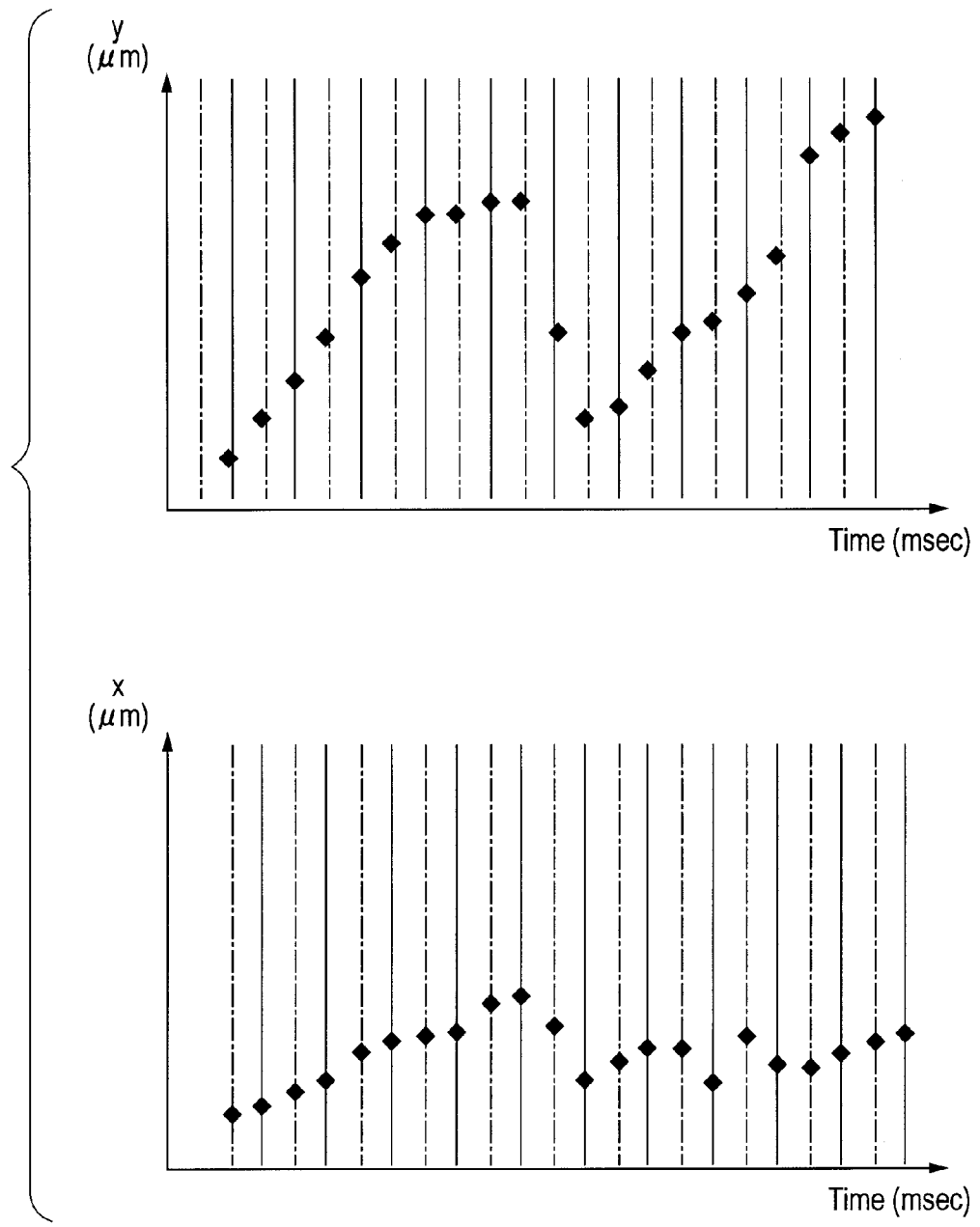
FIG. 6 is a schematic diagram in which values calculated from SLO images according to the second embodiment of the present invention are plotted.
Figure 7:
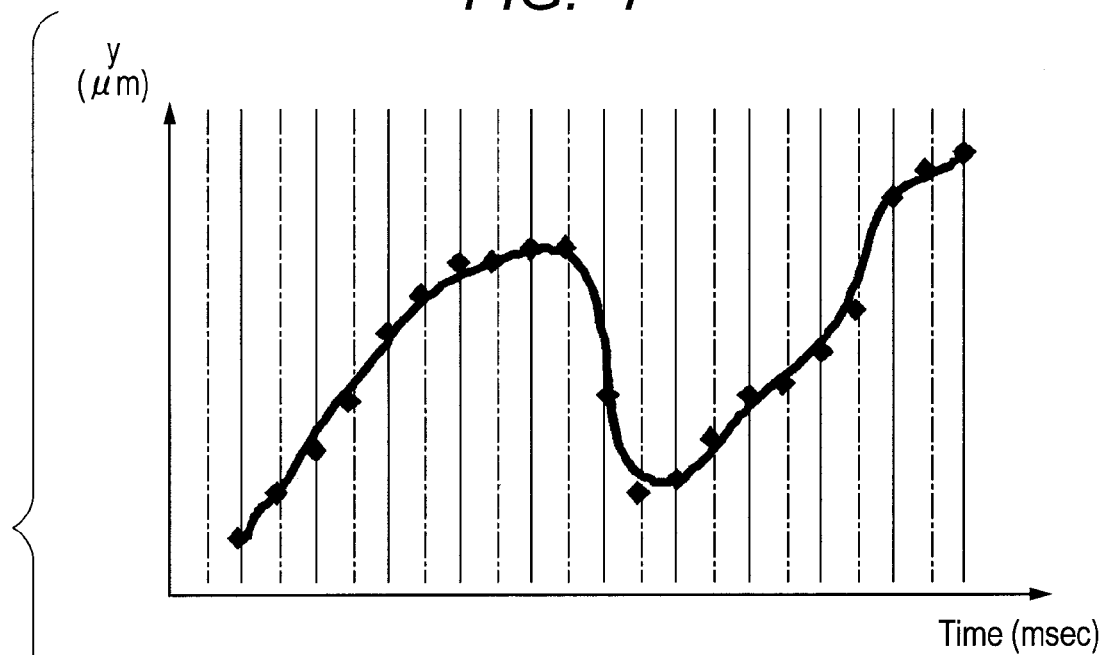
FIG. 7 is a schematic diagram of graphs according to the second embodiment of the present invention.
Figure 7:
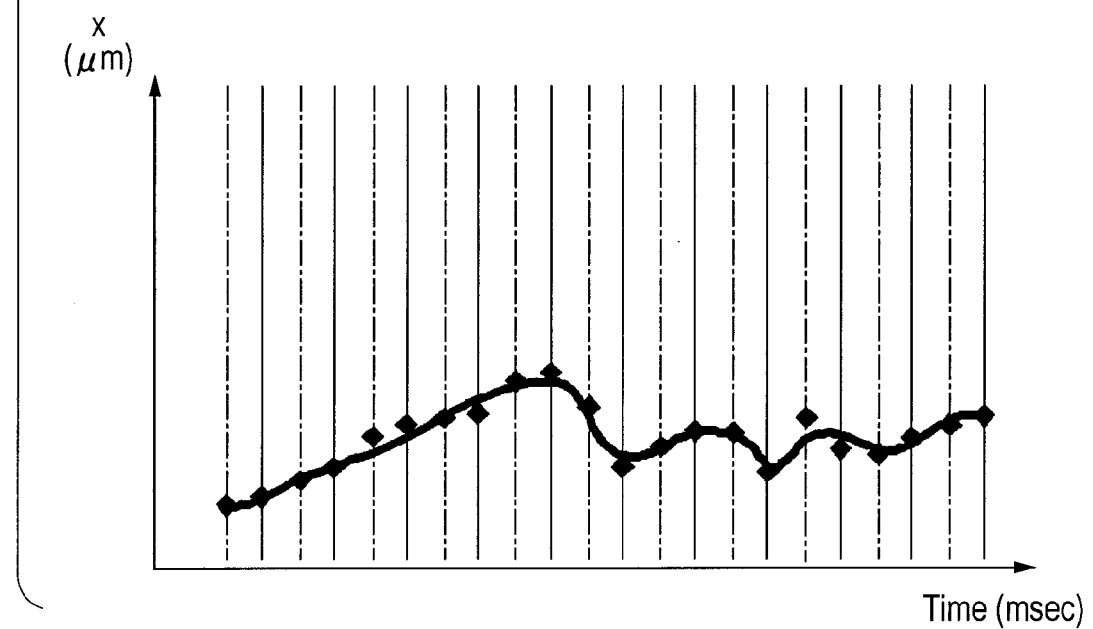

After the measurement is completed, the movement of the eyeball is calculated from each SLO image. The movement of the eyeball in the present embodiment is calculated by template matching. Two locations of the blood vessel to be feature points are extracted from initial SLO images. For example, T-1 and T-2 are feature points in the S-1' image. The amount of movement of the eyeball is calculated from template position information of each SLO image. Position information of the eyeball is obtained at 40 Hz. The amount of certain movement of the eyeball is represented as graphs regarding each of x and y. The result is shown in FIG. 6. FIG. 6 is interpolated (graph drawing) as shown in FIG. 7 by a portion of the CPU 201 functioning as a unit to draw a graph. Movement information drawn as a graph by the unit to draw a graph is displayed by the display device 206 functioning as a display unit. In the present embodiment, a graph is drawn by using polynomial approximation. By using information of FIG. 7, the position information of the eyeball of the OCT images (a) to (l) can be determined in the approximation in which drifts and micro saccade are reflected. The position information when an OCT image is acquired can be obtained from position information with respect to time. In the present embodiment, when the eyeball moves 100 μm or more in the y direction, the corresponding OCT image is not used for superimposition. In the present embodiment, movement of 1 μm/msec or more is determined to be micro saccade, which is automatically calculated from a graph to automatically remove the applicable OCT image from a set of images to be superimposed, but the user may also select OCT images that should not be used by the user for superimposition from a displayed graph.

A high-quality OCT image can be acquired by performing the above processing and superimposing OCT images.

In the present embodiment, the polynomial approximation is used in the interpolation method, but other interpolation methods such as the spline interpolation and linear interpolation may also be used.

Third Embodiment

In the first and second embodiments, position information of an OCT image for which no position information is present is determined by using position information of OCT images before and after the OCT image.

In the present embodiment, by contrast, position information of an OCT image is predicted from a plurality of pieces of position information immediately before the OCT image for which the position information is determined and if the difference of the predicted position information from the position information determined in the first embodiment is large, the determined position information is not used.

The apparatus configuration is the same as in the first embodiment and thus, a description thereof will not be repeated.

In FIG. 4, position information of the OCT images O-2 and O-4 is determined from the SLO images S-1 and S-2 respectively and position information of the OCT image O-2 is determined from the OCT images O-1 and O-3 and thus, a case where position information of the OCT image O-3 will be described.

First, position information of the OCT image O-3 is predicted from the position information of the OCT images O-1 and O-2. That is, if movement information matched with an OCT image (position in an OCT image) is not present, the position information of the OCT image having no matched movement information is predicted from position information of OCT images that are photographed before the OCT image having no matched movement information and are matched. The prediction operation is performed by a portion of the CPU 201 functioning as a predicting unit.

Next, position information of the OCT image O-3 is determined from the position information of the OCT images O-2 and O-4. A shift is determined by comparing the predicted position information and the determined position information and if the shift is within a preset range, the determined position information is matched and stored as the position information of the OCT image O-3. The operation to determine the shift is performed by a portion of the CPU 201 functioning as a comparison unit that compares the movement information predicted by the above predicting unit and the movement information obtained by the above calculation unit.

Accordingly, even when a major movement of the eye that cannot be predicted occurs while fundus images are photographed, whether such an image is appropriate for superimposition can be determined.

Other Embodiment

In the first embodiment, the OCT image corresponding to the position information obtained from the SLO image is O-2 in FIG. 4. Similarly, the OCT image corresponding to the next SLO image S-2 is O-4. In the first embodiment, position information is matched with an OCT image acquired in the latter half of scanning to acquire an SLIO image, but position information may be matched with an OCT image acquired in the first half of scanning.

In the second embodiment, the OCT image corresponding to the position information T-1 obtained from an SLO image is (a) in FIG. 5 and the OCT image corresponding to the position information T-2 obtained in the latter half of scanning is (b) in FIG. 5. Position information is matched with an OCT image acquired in the timing when the position information is obtained.

In each embodiment, an internal fixation lamp is used, but an external fixation lamp may also be used. When external fixation lamp is used, fixation is more unstable than when an internal fixation lamp is used. Further, the fundus photographing apparatus is not limited to SLO and may be a fundus camera or LSLO.

The position information determined by the above processing may be used not only for superimposition processing of images, but also when a three-dimensional tomogram of retina, that is, a three-dimensional tomographic image is created. When, for example, OCT images are acquired equidistantly in the y-axis direction, a three-dimensional tomographic image is constituted regardless of the movement of the eyeball, but a more accurate three-dimensional tomographic image can be acquired by performing the processing described in the embodiments to form an image in a proper position. In such a case, the three-dimensional tomographic image is formulated by a portion of the CPU 201 functioning as a formulation unit using a plurality of tomographic images matched with the above movement information. This operation is performed by determining three-dimensional position information obtained from movement information and using the three-dimensional position information.

In the first and second embodiments, the amount of movement of the eyeball is determined from SLO images and OCT images are matched and processing of non-matched OCT images is described and this can be applied when the amount of movement of the eyeball cannot be determined due to poor quality of a portion of SLO images (a major movement of the eye occurs when a certain SLO image acquired or the like).

In the first embodiment, the acquisition rate of tomographic images is an integral multiple of the acquisition rate of fundus images in view of data interpolation. However, if position information can be determined by drawing a graph like in the second embodiment, the rate of the OCT image pickup unit may not be an integral multiple of the rate of the SLO image pickup unit. An approximation that is different from the above approximation may be used for interpolation.

A similar effect can also be gained of the algorithm used for position detection not through template matching or optical flow.

The present invention is also realized by performing the following processing. That is, processing to supply software (program) realizing the function of the above embodiments to a system or apparatus via a network or various storage media, wherein a computer (or a CPU or MPU) of the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-052287, filed Mar. 10, 2011, which is hereby incorporated by reference herein in its entirety.

What is claimed is:

1. A photographing apparatus, comprising:
   a fundus image acquisition unit configured to acquire a plurality of fundus images of an eye to be inspected at different times;
   a tomographic image acquisition unit configured to acquire a plurality of tomographic images of the eye to be inspected at different times;
   a measuring unit configured to measure movement information of the eye to be inspected from the plurality of fundus images; and
   a matching unit configured to match the measured movement information and a part of the plurality of tomographic images,
   wherein an acquisition rate of the plurality of tomographic images of the tomographic image acquisition unit is larger than an acquisition rate of the plurality of fundus images of the fundus image acquisition unit, and
   wherein the measuring unit is configured to measure movement information of a non-matched tomographic image for which no corresponding fundus image is present, on the basis of the movement information of, among matched tomographic images for which a corresponding fundus image is present, the matched tomographic images temporally close to the non-matched tomographic image.

2. The photographing apparatus according to claim 1, further comprising a combining unit configured to combine the plurality of tomographic images on the basis of the measured movement information of the matched tomographic images and the measured movement information of the non-matched tomographic image.

3. The photographing apparatus according to claim 1, further comprising a formulation unit configured to formulate a three-dimensional tomographic image by using the plurality of tomographic images on the basis of the measured movement information of the matched tomographic images and the measured movement information of the non-matched tomographic image.

4. The photographing apparatus according to claim 3, wherein three-dimensional position information is determined from the movement information, and
   wherein the three-dimensional tomographic image is formulated on the basis of the determined three-dimensional position information.

5. The photographing apparatus according to claim 1, wherein the acquisition rate of the plurality of tomographic images of the tomographic image acquisition unit is an integral multiple of the acquisition rate of the plurality of fundus images of the fundus image acquisition unit.

6. The photographing apparatus according to claim 1, further comprising a display controlling unit configured to display on a display unit, as a graph, the measured movement information corresponding to the plurality of tomographic images.

7. The photographing apparatus according to claim 1, further comprising a predicting unit configured to predict movement information of the non-matched tomographic image on the basis of the measured movement information corresponding to the matched tomographic images temporally close to the non-matched tomographic image,
   wherein the matching unit is configured to match the non-matched tomographic image and the predicted movement information.

8. A control method of a photographing apparatus, the control method comprising:
   acquiring a plurality of fundus images of an eye to be inspected at different times;
   acquiring a plurality of tomographic images of the eye to be inspected at different times;
   measuring movement information of the eye to be inspected from the plurality of fundus images; and
   matching the measured movement information and a part of the plurality of tomographic images,
   wherein an acquisition rate of the plurality of tomographic images of the tomographic image acquiring is larger than an acquisition rate of the plurality of fundus images of the fundus image acquiring, and
   wherein movement information of a non-matched tomographic image for which no corresponding fundus image is present is measured on the basis of the movement information of, among matched tomographic images for which a corresponding fundus image is present, the matched tomographic images temporally close to the non-matched tomographic image.

9. A non-transitory recording medium recording a program that causes a computer to execute each step of the control method according to claim 8.

10. A photographing apparatus, comprising:
    a fundus image acquisition unit that acquires a plurality of fundus images of an eye to be inspected at different times;
    a tomographic image acquisition unit that acquires a plurality of tomographic images of the eye to be inspected at different times;
    a measuring unit that measures movement information of the eye to be inspected from the plurality of fundus images;
    a matching unit configured to match the measured movement information and a part of the plurality of tomographic images, wherein the measuring unit is configured to measure movement information of a non-matched tomographic image for which no corresponding fundus image is present, on the basis of the movement information of, among matched tomographic images for which a corresponding fundus image is present, the matched tomographic images temporally close to the non-matched tomographic image; and
    a display controlling unit configured to display on a display unit, as a graph, the measured movement information.

11. A control method of a photographing apparatus, comprising:
    acquiring a plurality of fundus images of an eye to be inspected at different times;
    acquiring a plurality of tomographic images of the eye to be inspected at different times;
    measuring movement information of the eye to be inspected from the plurality of fundus images;
    matching the measured movement information and a part of the plurality of tomographic images, wherein the measuring step measures movement information of a non-matched tomographic image for which no corresponding fundus image is present, on the basis of the movement information of, among matched tomographic images for which a corresponding fundus image is present, the matched tomographic images temporally close to the non-matched tomographic image; and
    displaying on a display unit, as a graph, the measured movement information.

12. A non-transitory recording medium recording a program that causes a computer to execute each step of the control method according to claim 11.

13. The control method according to claim 8, further comprising a step of combining the plurality of tomographic images on the basis of the measured movement information of the matched tomographic images and the measured movement information of the non-matched tomographic image.

14. The control method according to claim 8, further comprising a step of formulating a three-dimensional tomographic image by using the plurality of tomographic images on the basis of the measured movement information of the matched tomographic images and the measured movement information of the non-matched tomographic image.

15. The control method according to claim 8, further comprising a step of displaying on a display unit, as a graph, the measured movement information corresponding to the plurality of tomographic images.

16. The control method according to claim 8, further comprising a step of predicting movement information of the non-matched tomographic image on the basis of the measured movement information corresponding to the matched tomographic images temporally close to the non-matched tomographic image,
   wherein the non-matched tomographic image and the predicted movement information are matched.

17. A photographing apparatus, comprising:
   a fundus image acquisition unit configured to acquire a plurality of fundus images of an eye to be inspected at different times;
   a tomographic image acquisition unit configured to acquire a plurality of tomographic images of the eye to be inspected at different times;
   a measuring unit configured to measure movement information of the eye to be inspected from the plurality of fundus images;
   a matching unit configured to match the measured movement information and a part of the plurality of tomographic images; and
   a predicting unit configured to predict movement information of a non-matched tomographic image on the basis of the measured movement information corresponding to matched tomographic images temporally close to the non-matched tomographic image,
   wherein the matching unit is configured to match the non-matched tomographic image and the predicted movement information.

18. A control method of a photographing apparatus, the control method comprising:
   acquiring a plurality of fundus images of an eye to be inspected at different times;
   acquiring a plurality of tomographic images of the eye to be inspected at different times;
   measuring movement information of the eye to be inspected from the plurality of fundus images;
   matching the measured movement information and a part of the plurality of tomographic images; and
   predicting movement information of a non-matched tomographic image on the basis of the measured movement information corresponding to matched tomographic images temporally close to the non-matched tomographic image,
   wherein the non-matched tomographic image and the predicted movement information are matched.

19. A non-transitory recording medium recording a program that causes a computer to execute each step of the control method according to claim 18.

* * * * *